United States Patent [19]
Brasile

[11] Patent Number: 5,843,024
[45] Date of Patent: Dec. 1, 1998

[54] SOLUTION AND PROCESS FOR RESUSCITATION AND PREPARATION OF ISCHEMICALLY DAMAGED TISSUE

[75] Inventor: Lauren Brasile, Albany, N.Y.

[73] Assignee: Breonics, Inc., Schenectady, N.Y.

[21] Appl. No.: 649,200

[22] Filed: May 17, 1996

[51] Int. Cl.$^6$ .................................................. A61M 31/00
[52] U.S. Cl. ........................................................... 604/49
[58] Field of Search .............................. 604/4–6, 19, 27, 604/28, 48, 49–53; 435/1.1, 1.2; 128/898; 514/832, 921, 929

[56] References Cited

U.S. PATENT DOCUMENTS

| | | | |
|---|---|---|---|
| 4,686,085 | 8/1987 | Osterholm | 422/45 |
| 5,011,469 | 4/1991 | Buckberg et al. | 604/4 |
| 5,085,630 | 2/1992 | Osterholm et al. | 604/28 |
| 5,130,230 | 7/1992 | Segall et al. | 435/1 |
| 5,137,510 | 8/1992 | Van Deripe | 604/28 |
| 5,290,766 | 3/1994 | Choong | 514/23 |
| 5,385,821 | 1/1995 | O'Dell et al. | 435/1 |
| 5,395,314 | 3/1995 | Klatz et al. | 604/24 |
| 5,514,536 | 5/1996 | Taylor | 435/1.2 |
| 5,552,267 | 9/1996 | Stern et al. | 435/1.1 |
| 5,574,019 | 11/1996 | Segall et al. | 514/23 |
| 5,584,804 | 12/1996 | Klatz et al. | 604/24 |

*Primary Examiner*—Manuel Mendez
*Attorney, Agent, or Firm*—Hodgson, Russ, Andrews, Woods & Goodyear

[57] ABSTRACT

The invention discloses a process and resuscitation solution for inducing repair of ischemically damaged organs and tissues, to the degree that impairment of function can be reversed; and preventing further tissue damage during restoration of the circulation of the treated organ or tissue. The process comprises flushing the organ with the resuscitation solution according to the present invention at a warm temperature of about 28° C. to about 37° C. to remove accumulated blood and acidotic products from blood flow deprivation; and perfusing the flushed organ or tissue with the resuscitation solution, wherein the solution contains a novel combination of components to provide for (i) dilating of the blood vessels within the organ or tissue, (ii) reestablishing organ or tissue function by supplying trophic factors, (iii) restoring cellular integrity and function to the ischemically damaged organ or tissue, and (iv) reestablishing oxidative metabolism by readapting the ischemically damaged organ or tissue, surviving by anaerobic respiration, to an oxygenated resuscitation solution.

30 Claims, 5 Drawing Sheets

FIG. 1

SOLUTION AND PROCESS FOR RESUSCITATION AND PREPARATION OF ISCHEMICALLY DAMAGED TISSUE

FIELD OF THE INVENTION

The present invention relates generally to tissue and organ preservation, maintenance, and repair. More specifically, the present invention provides a process by which the integrity, function, and viability is restored in an ischemically damaged organ or tissue using a composition provided herein.

BACKGROUND OF THE INVENTION

There continues to be an extreme shortage of organs for transplantation. Currently, the major limiting factor in clinical transplantation is the persistent shortage of organs. For example, kidney transplantation is largely dependant upon the availability of organs retrieved from heart-beating cadaver donors. Additionally, a large and as yet untapped source of organs for transplantation are non-heart-beating cadavers. Non-heart-beating cadavers are accident victims who succumb at the site of an injury and those having short post-trauma survival times. In such cases, the reasons such organs are not used is because once the heart stops beating, the lack of circulating blood supply (warm ischemia) results in an injury cascade.

An organ marginally, but functionally, damaged by warm ischemia cannot tolerate further damage mediated by the hypothermia. Under the hypothermic conditions utilized to preserve organs intended for transplantation, the lipid bilayer experiences a phase-change and becomes gel-like, with greatly reduced fluidity. The essentially frozen lipid in the cell membranes negates the utilization of $O_2$, even in the presence of a high $O_2$-tension. The metabolic consequence is glycolysis, which is analogous to the state of anoxia. It has been described that below 18° C., hypothermia inhibits the tubular activity of the kidney and that at 4° C., the utilization of oxygen is approximately 5% of that at normothermia.

Hypothermic storage can also produce vasospasm and subsequent edema in an organ. Hypothermically preserved organs can experience glomerular endothelial cell swelling and loss of vascular integrity along with tubular necrosis; phenomenon attributable to the hypothermic conditions employed. Hypothermia can also inhibit the Na/K dependant ATPase and result in the loss of the cell volume regulating capacity. The loss of volume regulation is what causes the cellular swelling and damage. An ample supply of oxygen can actively diminish the amount of this swelling. Without adequate oxygen delivery, the anoxia leads to disintegration of the smaller vessels after several hours of perfusion. The lack of oxygen and the subsequent depletion of ATP stores mean that anaerobic glycolysis is the principal source of energy under traditional preservation conditions. The lack of molecular oxygen for oxidative phosphorylation which occurs in ischemia, leads to the accumulation of NADH and the depletion of ATP stores within the mitochondria. The subsequent loss of nucleosides is probably a very important factor in the failure of tissues subjected to warm ischemia and prolonged periods of cold ischemia to regenerate ATP after restoration of the blood supply. The inability to supply adequate oxygen has lead to the routine reliance on hypothermia for organ preservation.

Thus, ischemia (whether warm ischemia or cold ischemia) is an injury cascade of events that can be characterized as a prelethal phase, and a lethal phase. The prelethal phase produces harmful effects in three ways: hypoxia; malnutrition; and failure to remove toxic metabolic wastes. With the lack of circulating blood comes a lack of molecular oxygen. The resulting hypoxia induces depletion of energy stores such as the depletion of ATP stores in mitochondria. Depletion of ATP leads to cellular changes including edema, loss of normal cellular integrity, and loss of membrane polarity. The cellular changes, induces the lethal phase of ischemia resulting in accumulation of metabolic wastes, activation of proteases, and cell death.

The current perfusate solution that represents the state-of-the-art in hypothermic organ preservation, and provides for optimized organ preservation under hypothermic conditions, contains components which prevent hypothermic induced tissue edema; metabolites which facilitate organ function upon transplantation; anti-oxidants; membrane stabilizers; colloids; ions; and salts (Southard et al., 1990, Transpl. 49:251; and Southard, 1989, Transpl. Proc. 21:1195). The formulation of this perfusate is designed to preserve the organs by hypothermic induced depression of metabolism. While it minimizes the edema and vasospasm normally encountered during hypothermic storage, it does not provide for the utilization of a substantially expanded donor pool.

This is due to the fact that an organ or tissue, marginally, but functionally, damaged by warm ischemia cannot tolerate further damage mediated by the hypothermia. Even with just 30 minutes of ischemia, the posttransplant function of an organ can be compromised. For example, using organs from heart beating cadavers, the immediate nonfunction rate is estimated to be 25%; and within just 30 minutes of ischemia, the immediate nonfunction rate is increased to about 60%. Thus, 60% of the kidneys from non-heart-beating cadavers do not immediately function because of prelethal ischemic injury. Further, irreversible ischemic damage and injury is thought to occur to organs deprived of blood flow in just a few hours or less (Klatz et al., U.S. Pat. No. 5,395,314). Unless new sources of organs can be developed, the number of transplantation procedures will remain constant. Additionally, the donor pool cannot be substantially expanded because there is no process/system available to repair prelethal ischemic damage in warm ischemically damaged organs or tissues.

Recent efforts have focused on prevention of ischemic damage by resuscitation with a reperfusion with a solution immediately after interruption of the blood supply. For example, a protective solution, disclosed in U.S. Pat. No. 4,415,556, is used during surgical techniques or for organs to be transplanted for preventing ischemic damage to the organ. The protective solution is used as a perfusate to improve aerobic metabolism during the perfusion of the organ. U.S. Pat. No. 5,395,314 describes a method of resuscitating a brain by circulating, after interruption of the blood supply, through the brain a hypothermic preservation solution (approximately 8°–10° C.) designed to lower organ metabolism, deliver oxygen, and inhibit free radical damage.

Although such methods and preservation solutions are useful in preventing ischemic damage in organs, these beneficial effects are overshadowed by practical and functional limitations. First, for such methods and solutions to be effective in preventing ischemic damage, they must be applied immediately (within minutes) after interruption of the blood supply. Logistic restraints, for example in the case of an accident victim as an organ donor, may severely curtail the use of such methods and solutions to be practical in a hospital setting only. Secondly, irreversible ischemic damage and injury is thought to occur to organs deprived of blood flow in minutes (e.g., brain) or within just a few hours (heart, kidney). An organ or tissue, marginally, but functionally, damaged by warm ischemia cannot tolerate further damage mediated by hypothermic storage prior to transplantation, or restoration of blood flow upon transplantation. One reason is that restoration of the circulation after ischemia-reperfusion may paradoxically result in further tissue damage (McCord et al., 1985, N Engl J Med 312:159–163). Restoration of the circulation results in reoxygenation of the injured tissue. Reoxygenating ischemically damage tissue can result in further tissue injury caused through the formation of oxygen-free radicals, depletion of free radical scavengers, and the release of chemotactic agents.

Thus, there is a need for a process and solution which can overcome, rather than only inhibit, the effects of ischemia in organs or tissues during the prelethal phase, and support a repair process in organs or tissues in the very early stages of lethal ischemia. A process for inducing repair of ischemically damaged organs and tissues, to the degree that impairment of function can be reversed, and the prevention of further tissue damage during restoration of the circulation, may lead to the organ donor pool being substantially expanded.

SUMMARY OF THE INVENTION

The present invention addresses what, up to the time of the invention, was thought to be irreversible ischemic damage and injury to organs or tissues deprived of blood flow. The process and compositions are used after ischemic damage and injury for inducing repair of ischemically damaged organs and tissues, and the prevention of further tissue damage during restoration of the circulation. This distinguishes the process and compositions according to the present invention from currently used methods and compositions directed to use before ischemic damage and injury, with the intended purpose of preventing or inhibiting such damage. The process according to the present invention is a process by which the integrity and function of an ischemically damaged organ or tissue can be reestablished, during at least the prelethal phase of ischemia, using a resuscitation solution according to the present invention. Further, the process and solution according to the present invention are intended to prevent or inhibit further tissue damage which can be induced during restoration of the blood circulation in an organ or tissue deprived of blood flow.

The process according to the present invention comprises flushing the organ through the arterial system with the resuscitation solution according to the present invention at a warm temperature of about 28° C. to about 37° C. to remove blood and acidotic products which have accumulated in the organ or tissue during the period of blood flow deprivation; and perfusing the flushed organ or tissue with the resuscitation solution to (i) dilate the blood vessels, particularly constricted microvessels, within the organ or tissue, (ii) reestablish organ or tissue function by supplying trophic factors, (iii) restore cellular integrity and function to the ischemically damaged organ or tissue, and (iv) reestablish oxidative metabolism by readapting the ischemically damaged organ or tissue, surviving by anaerobic respiration, to an oxygenated resuscitation solution; in rendering the organ or tissue suitable for transplantation and/or for restoration of the blood circulation.

DETAILED DESCRIPTION OF THE PREFERRED EMBODIMENTS

Definitions

"Deprived of blood flow" is a term used hereinafter for the purposes of the specification and claims to refer to the cessation of blood circulation through an organ or a tissue in any circumstance in which blood circulation may be ceased and warm ischemia ensues. This includes stopping of the heart beat for surgical procedures, or because of natural causes such as in a heart attack.

"An organ or tissue" is a term used hereinafter for the purposes of the specification and claims to refer to an "organ" including, but not limited to kidney, heart, liver, lung, small bowel, pancreas, brain, eye, and skin.

"Resuscitation solution" is a term used hereinafter for the purposes of the specification and claims to refer to a buffered physiologic solution that provides means for reestablishment of integrity and function in ischemically damaged and injured organs deprived of blood flow, and for prevention or inhibition of further tissue damage which can be induced during restoration of the blood circulation in an organ deprived of blood flow.

The process according to the present invention is a process by which the integrity and function of an ischemically damaged organ can be reestablished, during at least the prelethal phase of ischemia, using a resuscitation solution according to the present invention. Reestablishment of organ integrity and function using the process and compositions according to the present invention was unexpected since it was thought, at the time of the invention, that ischemic damage and injury to organs deprived of blood flow for just a few hours or less was irreversible. Further, the process and solution according to the present invention are intended to prevent or inhibit further tissue damage which can be induced during restoration of the blood circulation in an organ deprived of blood flow.

The process and solution according to the present invention provides a means to remove blood and acidotic products accumulated during the period of blood flow deprivation of the organ; a means to reestablish cellular integrity and function, thereby restoring organ function; and a means for readapting the organ to an oxygenated environment. The ability to reestablish function in an organ following ischemic damage and injury was found possible based on the premises that (1) blood does not coagulate while in contact with viable vascular endothelial cells, and therefore ischemically damaged organs can be reperfused providing such endothelium is still viable and intact; (2) reestablishing vascular dynamics is dependent upon providing adequate endothelial cell-dependent vasodilation in order to adequately perfuse and oxygenate the tissue and provide for normal auto-regulator mechanisms; (3) the microvessels must be adequately dilated for resuscitation, but normal permeability can not be altered in order for the cellular integrity to be restored; and (4) trophic factors, lost during ischemia, must be restored, and cellular polarity established for function to be regained.

Figure 1:
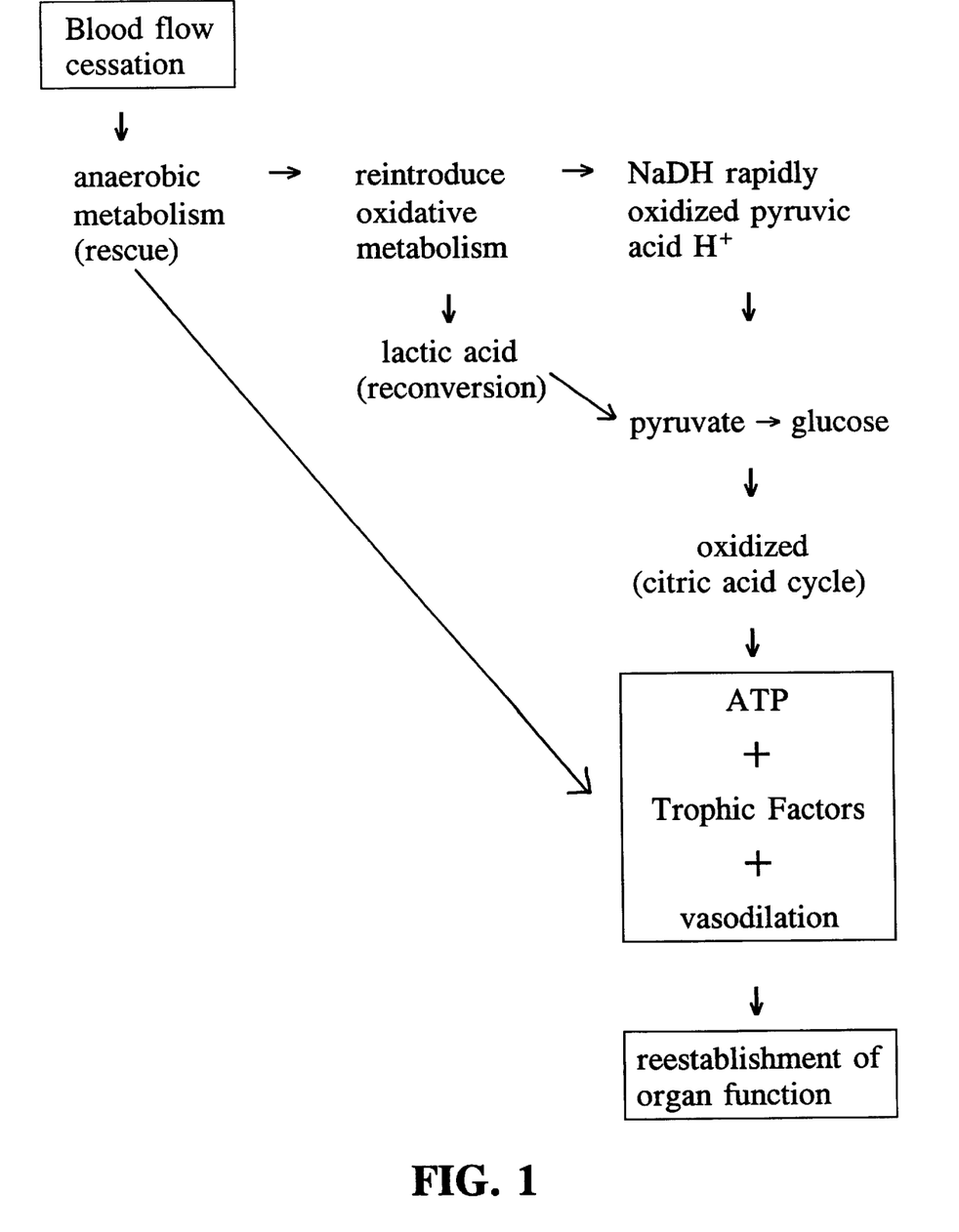
FIG. 1 is a flowchart showing the organ processes affected by the resuscitation process and solution according to the present invention.

The process and solution according to the present invention work together to resuscitate an ischemically damaged organ for the purposes of restoring organ function and for readapting the organ to an oxygenated environment. FIG. 1 is a flowchart showing the organ processes affected by the resuscitation process and solution according to the present invention.

The following examples illustrate the preferred embodiments of the practice of the invention. In the following embodiments used to illustrate the invention, it is important to consider the following concept. The bovine calf model and the canine model have been validated for evaluation of compositions and methods related to organ transplantation intended for humans because the models have been shown to reflect a physiological basis. Thus, while the composition and method according to the present invention have been validated in these experimental models, the composition and method are to be utilized primarily in humans. A physiological basis for scale-up from the experimental models to humans is known to those skilled in the art, and includes consideration of differences such as organ volumes and organ flow rates (See for example, Harrison et al., 1977, *J. Pharm. Sci.* 66:1679–1683). It should be understood that these examples are intended as illustrations, and not limitations.

EXAMPLE 1

The Process

The process according to the present invention involves interceding during a window of blood flow deprivation in an organ before substantial cell death occurs. It can be appreciated by those skilled in the art that the window in which the process can be used varies on the organ type to be treated. For example, the window for treatment of a heart using the process according to the present invention may be less than approximately one hour; whereas a kidney can be treated using the process within a time period up to approximately 4 hours of blood flow deprivation. In order to halt the ischemic injury cascade from leading to cell death, and in a manner as illustrated in FIG. 1, the process according to the present invention comprises the steps of:

(1) Flushing the ischemically damaged organ through the arterial system with the resuscitation solution according to the present invention at a warm temperature of about 28° C. to about 37° C. to
  (i) remove blood and acidotic products which have accumulated in the organ during the period of blood flow deprivation;
  (ii) restore the cellular environment to a physiologic pH;
  (iii) adequately dilate the microvessels;
  (iv) support the ongoing anaerobic metabolism as a rescue procedure by providing high energy compounds and supporting glycolysis with supplemental substrates that may include, but are not limited to glucose, pyruvate, and uridine 5'-triphosphate (UTP);
  (v) initiate a conversion from anaerobic metabolism to oxidative metabolism by providing metabolic substrates to restore the adenine compound pool, support the citric acid cycle, and to reestablish coupling of the electron transport chain, whereby molecular oxygen is slowly introduced to prevent a reperfusion injury mediated by oxygen toxicity;
  (vi) provide a mechanism to adequately vasodilate the microvessel endothelial cell bed within a severely constricted, edematous, ischemically damaged organ, without substantially altering the permeability of the organ, and wherein the vasodilation allows for adequate perfusion of the organ tissue which provides a stable perfusion pressure, stable flow rates, and constant temperature, constant pH, and constant oxygenation;
  (vii) provide trophic factors to reestablish function in the ischemically damaged organ, thereby providing metabolites for recovering cellular integrity and function; and
2) Perfusing the ischemically damaged organ through the arterial system with the resuscitation solution according to the present invention at a warm temperature of about 28° C. to about 37° C. to
  (i) normalize oxygenation, temperature, and pH;
  (ii) continue to provide a mechanism to adequately vasodilate the vasculature of the organ, without substantially altering the permeability of the organ, thereby resulting in stable perfusion pressure, and stable vasculature flow rates; and
  (iii) continue to provide trophic factors to reestablish function in the ischemically damaged organ, thereby providing metabolites for recovering cellular integrity and function such as tightening cellular junction and reestablishing membrane polarity.

It will be appreciated by those skilled in the art, that one or more of the benefits derived during the flushing step will also be continued in the perfusion step, as the resuscitation solution according to the present invention may be used during the whole process, i.e, including both the flushing and perfusing steps.

For purposes of illustration, and not limitation, in the flushing step a sufficient amount of the resuscitation solution is slowly introduced by infusion via a cannula into the major arterial blood supply for that particular organ until the effluent is free of blood. In this way, ischemic blood and acidotic products, which have accumulated in the vascular space during the period that the organ is deprived of blood flow, are removed from the vascular space. Further, pH is restored and fresh substrate is delivered to support anaerobic metabolism and other cellular pathways necessary for cellular integrity and function. It will be appreciated by those skilled in the art that the amount of the resuscitation solution sufficient for use in the flush may depend on the particular organ type and size to be flushed, as well as the length of time of blood flow deprivation. By way of illustration, but not limitation, 200 to 600 ml of the resuscitation solution may be a sufficient amount to flush a human kidney which has been deprived of blood flow for a period of 1–3 hours.

For purposes of illustration, and not limitation, in the perfusion step a sufficient amount of the resuscitation solution is slowly perfused at a systolic pressure appropriate for the ischemically damaged organ being resuscitated, until a flow rate is achieved which is near normal for that particular organ type. By way of illustration, but not limitation, a human kidney which has been deprived of blood flow for a period of 1–3 hours may be slowly perfused with the resuscitation solution at a systolic pressure of <80 mmHg, until a flow rate of >50 ml/min is achieved. The pH is normalized into physiologic range by slowly introducing molecular oxygen via an oxygenator, or via an oxygen transporting compound as a component in the resuscitation solution. Oxygenation of the organ during perfusion, as well as normalization of temperature and pH, occurs within about the first 15–30 minutes of perfusion. As the organ slowly vasodilates, perfusion pressures and flow rates begin to stabilize, and the organ quickly switches to oxidative metabolism. It is appreciated by those skilled in the art that the length of time necessary for perfusion depends on the particular organ type and size being perfused, as well as the length of time of blood flow deprivation. However, treatment of an ischemically damaged organ with the process (flushing and perfusing) according to the present invention for approximately 2 hours may be sufficient in the resuscitation of most organs (e.g., deprived of blood flow for between 0.5 to 4 hours) for resumption of organ function. Also, if the organ produces a product, such as a kidney produces urine, the process can result in the production of a normal product of organ function.

The process according to the present invention has been developed to preserve and resuscitate ischemically damaged organs ex vivo without traditional hypothermia (4°–10° C.). The process provides the necessary oxygen delivery, nutrients for metabolism, oncotic pressure, pH, perfusion pressures, and flow rates to support organ metabolism ex vivo, most often within or near the respective normal range in vivo. A near normal rate of metabolism is defined herein as about 70%–90% of the range of normal rates of metabolism. Further, the process according to the present invention supports a level of metabolism ex vivo which provides enough oxidative metabolism to result in the normal functional product of the organ. The development of this process which supports organs ex vivo, without traditional hypothermia, presents the opportunity to support a near normal rate of metabolism and to establish functional capabilities which can be correlated with postsurgical or post-transplantational course.

In a further embodiment, the process according to the present invention can be performed using a device comprising a laminar or pulsatile pumping system to deliver the resuscitation solution, including means for providing and controlling perfusion and the perfusion pressure; means for temperature control; and means for providing and controlling introduction of, and venting of, respiratory gases. Such a device has been described by the present inventor in U.S. Ser. No. 08/246,801, which is herein incorporated by reference. Such a device may also include a device means for testing and/or collecting perfusate which has already circulated through the organ to monitor and measure one or more functional characteristics such as pH, various pressures, flow rate, vascular resistance, various chemical constituents, oxygenation, carbon dioxide concentration, and oxygen consumption. Further, the device means or a second device means in conjunction with the device, may be used to measure and/or collect organ product diverted from the organ, such as urine from a kidney, wherein subsequent measurement of parameters of the organ product can relate to organ integrity and function during or subsequent to the process according to the present invention.

EXAMPLE 2

The Resuscitation Solution

Organ preservation and perfusate solutions are known in the art as comprising a base solution that consists of a buffered physiological solution, such as a salt solution or a cell culture-like basal medium, to which is added a variety of defined supplements. In a preferred embodiment, the resuscitation solution of the present invention also employs such a base solution containing amino acids, ions, physiologic salts, impermeants, serum proteins and/or factors, and sugars. In addition to the components of the base solution, the resuscitation solution of the present invention contains a novel combination of supplements that can be grouped in at least 3 component categories. It can be appreciated by those skilled in the art that the components in each category may be substituted with a functionally equivalent compound to achieve the same result. Thus, the following listed species of components in each component category is for purposes of illustration, and not limitation.

A first component category, vasodilators, comprises a combination of components in a physiologically effective amount which provide a means to adequately dilate large vessels via smooth muscle cell relaxation, as well as to adequately dilate microvessels. To insure that normal permeability of the vasculature is maintained, the vasodilation is controlled in an endothelial cell-dependent manner. Such a combination of components may include (i) substrates for endothelial cell mediated vasodilation, such as acetylcholine, dopamine, bradykinin, and arginine; (ii) substrates for microvessel vasodilation, such as prostacyclin (and analogues, e.g., carbacyclin) and $Mg^+$; and (iii) adenosine (and analogues, e.g. cyclohexyladenosine), and verapamil for their combined effects on vascular dilation mediated by calcium channel blocking (other calcium channel blockers include flunarizine, nifedipine, SNX-11, chlorpromazine, and diltiazem). The result of using such a combination of vasodilators is that the vasculature is well dilated while simultaneously retaining its integrity and normal barrier function. The vasodilators comprise from about 1% to about 50% by volume (w/v) of the novel combination of supplements which are added to the base solution in forming the resuscitation solution of the present invention.

A second component category, chemical energy substrates, comprises a combination of components in a physiologically effective amount which provide a means to reestablish oxidative metabolism which are lost during the period of blood flow deprivation. During blood flow deprivation, the resulting loss of membrane integrity leads to loss of intracellular components such as ions, components of the adenine compound pool, of the citric acid cycle, and of the coupled electron transport chain. Such chemical energy substrates added to the resuscitation solution may include pyruvate; glucose; ATP; AMP; coenzyme A; β-nicotinamide adenine dinucleotide ($NAD^+$); β-nicotinamide adenine dinucleotide phosphate ($NADP^+$); flavin adenine dinucleotide (FAD); thiamine pyrophosphate chloride (cocarboxylase); uridine 5' triphosphate (UTP); chloride; adenosine; magnesium; and a combination thereof. If the supply of energy is reestablished in tissue cells before the death of the cells occurs, cellular changes during the blood flow deprivation period can be reversed, and the tissue cell volume returns to normal. The chemical energy substrates comprise from about 0.01% to about 90% by volume of the novel combination of supplements which are added to the base solution in forming the resuscitation solution of the present invention.

A third component category, trophic factors, comprises a combination of components in a physiologically effective amount which provide a means to promote one or more cellular repair processes to reestablish cellular function lost during the period of blood flow deprivation. The combination of trophic factors provides a means to promote protein synthesis leading to reestablishment of tighter cellular junctions and regeneration of membrane polarity, thereby leading to recovery of cellular function. Such trophic factors added to the resuscitation solution can include a high concentration amino acids and magnesium (e.g., 2 to 6 times the typical plasma concentration), nucleic acid derivatives, and ribonucleosides; and growth factors with membrane potentiators, such as acidic fibroblast growth factor (FGF), basic FGF, heparin and chondroitin sulfate, and combinations thereof. The trophic factors comprise from about 1% to about 90% by volume of the novel combination of supplements which are added to, and dissolved in, the base solution in forming the resuscitation solution of the present invention.

It will be appreciated by those skilled in the art that components in any one or more of the three component categories can have additional functions desirable for the process according to the present invention. For example, magnesium ions (introduced as part of a magnesium carrying compound) acts as both a vasodilator and a chemical energy substrate; and glucose acts as both a trophic factor and chemical energy substrate. Further, in a preferred embodiment, amino acids contained in the resuscitation solution include cystine and cysteine in amounts which, besides functioning as trophic factors, also function as antioxidants- preferred free radical scavengers which scavenge toxic free radicals during the flushing and perfusing steps of the process. Other antioxidants, such as glutathione, cyclodextrin, superoxide dismutase (SOD), catalase, chlorpromazine, and prostacyclin may be included, or used as functionally equivalent compounds, in the resuscitation solution of the present invention. Such antioxidants comprise from about 0.000% to about 10% by volume of the novel combination of supplements which are added to, and dissolved in, the base solution in forming the resuscitation solution of the present invention.

In another embodiment of the present invention, wherein the tissue to be resuscitated using the resuscitation solution according to the present invention involves neurological tissue (e.g., brain), the resuscitation solution may further comprise neuroprotective drugs such as NMDA receptor-blocking agents (NMDA receptor ion-channel blockers, e.g., Aptiganel and Cerestat; NMDA receptor glycine-site blockers, e.g. ZD 9379 and GV 150-562A), blockers of nitric oxide (NO) accumulation (e.g., lubeluzole), and sodium channel blockers to inhibit the influx of sodium into cells which can trigger glutamate release (e.g., BW619-C89, fosphenytoin).

In another embodiment of the present invention, rather than introducing molecular oxygen via an oxygenator in the process, the resuscitation solution contains one or more oxygen transporting compounds ("oxygen carrying agents") that function to provide molecular oxygen for oxidative metabolism to the ischemically damaged and injured organ. Such oxygen carrying agents are known to those skilled in the art to include, but are not limited to, hemoglobin, stabilized hemoglobin derivatives (made from hemolyzed human erythrocytes such as pyridoxylated hemoglobin), polyoxethylene conjugates (PHP), recombinant hemoglobin products, perfluorochemical (PFC) emulsions and/or perfluorochemical microbubbles (collectively referred to as "perfluorochemical"). Such oxygen carrying agents comprise from about 0.000% to about 50% by volume of the novel combination of supplements which are added to, and dissolved in, the base solution in forming the resuscitation solution of the present invention; or about 0.000% to about 20% of the total resuscitation solution (v/v).

PFC emulsions said to be useful as oxygen carrying agents are described, for example, in U.S. Pat. Nos. 5,403,575; 4,868,318; 4,866,096; 4,865,836; 4,686,024; 4,534,978; 4,443,480; 4,423,077; 4,252,827; 4,187,252; 4,186,253; 4,110,474; and 3,962,439. Such liquid PFC emulsions include, but are not limited to perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinolidizine, 9 to 12 carbon perfluoro amines, perfluorodecalin, perfluoroindane, perfluorotrimethyl bicyclo[3,3,1] onane, perfluoromethyl adamante, perfluorodimethyl adamantane. PFC microbubbles that may be useful as oxygen carrying agents are described, for example, in U.S. Pat. No. 5,409,688 and U.S. Pat. No. 5,393,524. PFCs that are disclosed as being useful for creating such microbubbles include, but are not limited to, dodecafluoropentane (DDFP), sulfur hexafluoride, pentane, hexafluoropropylene, octafluoropropane, hexafluoroethane, octafluoro-2-butyne, hexafluorobuta-1,3-diene, isoprene, octafluorocyclobutane, decafluorobutane, cis-2-pentene, dimethyl sulfide, ethylarsine, bromochlorofluoromethane, trans-2pentene, 2-chloropropane, hexafluorodisulfide, ethylmercaptan, diethylether, ethylvinylether, valylene, trisfluoroarsine, furfuyl bromide, cis-propenyl chloride, bytyl fluoride, 1,1 dichloroethane, isopropyl methyl ether, isopropylamine, methylfomate, 2-acetyl-furan, ethylenefluoride, 1-pentene, isopropylacetylene, perfluoropentane, isopentane, vinyl ether, 2-butyne, 1,4-pentadiene, tetramethyl silane, dimethyl phosphine, dibromodifluoromethane, 2-chloro-propene, difluroiodomethane, acetaldehyde, trimethyl boric, 3-methyl-2-butene, 1,1 dimethylcyclopropane, aminoethane, vinyl bromide, disilanomethane, trichlorofluoromethane, bromofluoromethane, trifluorodichloroethane, perfluoropentene, and other fluorine containing hydrocarbons (U.S. Pat. No. 5,409,688).

In a process for preparing the resuscitation solution according to the present invention, to a base solution is added and dissolved therein a novel combination of supplements that can be grouped in at least 3 component categories comprising vasodilators, chemical energy substrates, and trophic factors. Although the composition of the resuscitation solution, for use with the process according to the present invention, can vary by component and component ranges as previously described, a preferred formulation is set forth below in Table 1 for purposes of illustration and not limitation (note that a component which can function in more than one of the at least 3 component categories is placed in one category below, for purposes of clarity).

TABLE 1

Supplement added to Base Solution
(Amounts are milligrams per liter of Base solution)

| Vasodilators | Amount |
| --- | --- |
| arginine | 140 |
| acetylcholine | 2 |
| verapamil | 0.2 |
| prostacyclin | 0.06 |
| magnesium | 600 |
| Chemical Energy Substrates | |
| ATP | 2 |
| AMP | 2 |
| UTP | 4 |
| Coenzyme A | 10 |

TABLE 1-continued

Supplement added to Base Solution
(Amounts are milligrams per liter of Base solution)

| Vasodilators | Amount |
| --- | --- |
| diphosphopyridine nucleotide | 28 |
| FAD | 4 |
| triphosphopyridine nucleotide monosodium | 4 |
| cocarboxylase | 4 |
| Trophic Factors | |
| acidic &/or basic FGFs | 200 |
| pyruvate | 220 |
| glucose | 2,000 |
| heparin | 180 |
| insulin | 10 |
| (Nucleic Acid derivatives) | |
| deoxyadenosine | 40 |
| deoxyguanosine | 40 |
| deoxycytidine | 40 |
| thymidine | 40 |
| (Ribonucleotides) | |
| adenosine | 40 |
| cytidine | 40 |
| guanosine | 40 |
| uridine | 40 |

The resuscitation solution thus prepared should have a osmolarity >330 mOsm but preferably less than 600 mOsm, and in a preferable range of about 350 mOsm to about 400 mOsm. The pH of the resuscitation solution should be adjusted to a pH within a pH range of about 6.5 to about 7.5, and preferably in a pH range of 7.3 to 7.45.

As pointed out, in another embodiment the resuscitation solution may further comprise additional antioxidants, and one or more oxygen carrying agents as follows (per liter of base solution):

| Antioxidants | Amount |
| --- | --- |
| Glutathione | .1 mg |
| cyclodextrin | 500 mg |
| Oxygen carrying agent | |
| perfluorochemical | 20% v/v |

EXAMPLE 3

Effect of Blood Deprivation

Experiments were conducted to show the effect of warm ischemia, caused by depriving an organ of blood flow for approximately 30 minutes. Such warm ischemia leads to rapid deterioration in cellular integrity. The ischemic injury cascade starts with the loss of adenine compound pool, leading to edema. The loss of the cellular integrity and the occurrence of edema results in the collapse of the vascular integrity and loss of normal permeability function. In an organ such as a kidney, the ischemic injury caused by depriving the kidney of blood flow for just 30 minutes can be seen to cause profound vasoconstriction. The profound vasoconstriction results in inadequate flow rates to adequately perfuse the kidney. High vascular resistance, in vasoconstricted vessels, leads to further deterioration with secondary anoxia, thereby leading to a loss of functional capability (i.e., lack of urine production). Table 2 illustrates a comparison of perfusion characteristics (pressure; flow rate; and vascular resistance) and organ function (urine production) in an experimental animal model system comprising bovine calf kidneys which have not been deprived of blood flow ("normal"), and bovine calf kidneys deprived of blood flow for just 30 minutes ("ischemic"). Vascular resistance is mean pressure/mean flow rate.

TABLE 2

| Parameters | Normal | Ischemic |
| --- | --- | --- |
| number of kidneys | 25 | 5 |
| mean pressure | 50/30 | 44/40 |
| mean flow rate | >95 cc/min | 12.9 cc/min |
| mean vascular resistance | 0.4 | 3.26 |
| urine production | yes | no |

EXAMPLE 4

Effects of the Resuscitation Process and Solution

Experiments were conducted to show the ability of the process and resuscitation solution according to the present invention to overcome, rather than only inhibit, the effects of warm ischemia in organs, and support a repair process to the degree that impairment of organ function can be reversed. Kidneys were procured from euthanized bovine calves. At 30 minutes or 60 minutes of blood flow deprivation, the kidneys were removed by midline incision. No treatment was given prior to removing the kidneys, including no administration of anticoagulants. Each control kidney experienced 30 minutes of blood flow deprivation thereby suffering ischemic injury for that period. The control kidneys, after removal, were flushed with 100 cc of a basal cell culture medium at a temperature of 32° C., so that the kidneys were flushed of the blood remaining in their respective vascular compartment. Each test kidney experienced 60 minutes of blood flow deprivation thereby suffering ischemic injury for that period. The test kidneys, after removal, were flushed with 100 cc of the resuscitation solution according to the present invention at a temperature of 32° C. After flushing, the respective kidneys were pumped on a modified MOX-100™ transport preservation system. The control kidneys were pumped at 32° C., using technology previously developed to preserve organs using warm preservation technology, using the basal cell culture medium as a perfusate. The test kidneys were pumped using the process and resuscitation solution according to the present invention, at 32° C. A comparison of the perfusion characteristics (pressure; flow rate; and vascular resistance) and organ function (urine production) of the control group (30 minutes w/o invention) with the test group (60 minutes w/invention) is illustrated in Table 3.

TABLE 3

| Parameters | 30' w/o invention | 60' w/invention |
| --- | --- | --- |
| number of kidneys | 5 | 16 |
| mean pressure | 44/40 | 54/25 |
| mean flow rate | 12.9 cc/min | 97.4 cc/min |
| mean vascular resistance | 3.26 | 0.47 |
| urine production | none | yes |

The test kidneys, after suffering ischemic damage for a period of one hour, which were then resuscitated with the process and resuscitation solution according to the present invention, demonstrated perfusion characteristics (pressure; flow rate; and vascular resistance) and organ function (urine production) within the functional ranges of the normal kidneys illustrated in Table 2. Thus, demonstrated is the ability of the process and resuscitation solution according to the present invention to overcome, rather than only inhibit, the effects of warm ischemia in organs, and support a repair process to the degree that impairment of organ function can be reversed.

EXAMPLE 5

Effectiveness with varying injury times

Experiments were conducted to evaluate the effects of the process and resuscitation solution according to the present invention in organs which have been deprived of blood flow for time periods greater than 1 hour. Bovine calf kidneys were removed from euthanized calves at various time periods of blood flow deprivation including 60 minutes, 90 minutes, 2 hours, or 4 hours. No treatment was given prior to removing the kidneys, including no administration of anticoagulants. Each kidney was then flushed with 100 cc of the resuscitation solution according to the present invention at a temperature of 32° C. In no case were any of the kidneys found to have clotted blood in the vascular compartment. The blood appears to remain fluid as long as it is in contact viable vascular endothelium. After flushing, the respective kidneys were pumped for several hours using the process and resuscitation solution according to the present invention, at 30° C. A comparison of the mean perfusion characteristics (pressure; flow rate; and vascular resistance) and organ function (urine creatinine concentration- creatinine clearance; histology) of kidneys deprived of blood flow for 60 minutes (60'), kidneys deprived of blood flow for 90 minutes (90'), kidneys deprived of blood flow for 2 hours (120'), and kidneys deprived of blood flow for 4 hours (240') is shown in Table 4.

TABLE 4

| Parameter | 60' (N = 16) | 90' (N = 5) | 120' (N = 5) | 240' (N = 2) |
|---|---|---|---|---|
| pressure (mmHg) | 54/25 | 58/37 | 55/37 | 52/40 |
| flow rate (cc/min) | 97.4 | 72 | 68.6 | 36.5 |
| vascular resistance | 0.47 | 0.67 | 0.73 | 1.27 |
| creatinine (mg/dl) | 41.8 | 22.9 | 18.5 | 23.5 |
| histology | well preserved | well preserved with focal flattening of epithelium | overall good; focal edema | early focal necrosis |

The results demonstrate that the process and resuscitation solution according to the present invention can resuscitate an ischemically damaged organ at time periods of at least up to 4 hours of blood flow deprivation. For example, when a kidney, having suffered 60 minutes of warm ischemic injury, is pumped for 2 hours using the process and resuscitation solution, the perfusion characteristics are equivalent to those in normal kidneys as listed in Table 1. Histological evaluations support the functional data, as tissue sections examined show that morphology and integrity appear well preserved.

At 90 minutes and 120 minutes of blood flow deprivation, those kidneys reflect a more extensive cellular impairment (i.e., elevated diastolic pressures and reduced flow rates) than kidneys deprived of blood flow for 60 minutes. However, despite such cellular impairment, these kidneys still produced urine; and histologically they appeared well preserved. Additionally, necrosis was not detected in these kidneys.

Kidneys deprived of blood flow for 4 hours exhibited substantially reduced flow rates, with a concomitant elevation in diastolic pressures that includes constriction in the microvessel beds. However, it is important to point out that these kidneys still exhibited organ function. Urine was produced with a urinary creatinine concentration of 23.5 mg/dL. Histologically, these kidneys showed the first signs of focal, early necrosis. Mitotic characters were observed adjacent to the areas of focal tubule necrosis, indicating that an active repair process appears to have been initiated. Thus, even after 4 hours of blood flow deprivation, demonstrated is the ability of the process and resuscitation solution according to the present invention to overcome, rather than only inhibit, the effects of warm ischemia in organs, and support a repair process to the degree that impairment of organ function can be reversed.

It is important to note that control kidneys (without treatment with the process and resuscitation solution according to the present invention) were evaluated histologically after either 2 or 4 hours of blood flow deprivation in order to determine the relative benefit of the process and resuscitation solution. The histological evaluation of control kidneys suffering 2 hours of warm ischemia showed early diffuse tubular necrosis. At 4 hours of warm ischemic damage, control kidneys showed diffuse breakdown of the tubule cells. In contrast, in kidneys suffering 2 hours of warm ischemia, and then treated with the process and resuscitation solution according to the present invention, showed reestablished cellular integrity. Further, kidneys suffering 4 hours of warm ischemia, and then treated with the process and resuscitation solution according to the present invention, only showed focal tubule necrosis, as compared to widespread tubule damage in the control kidneys. The histologic evaluations further support the substantial efficacy of the process and resuscitation solution according to the present invention in reversing the cascade of warm ischemia events after blood flow deprivation.

EXAMPLE 6

In Vivo Function Of A Resuscitated Organ

A. Allotransplantation

Figure 2:
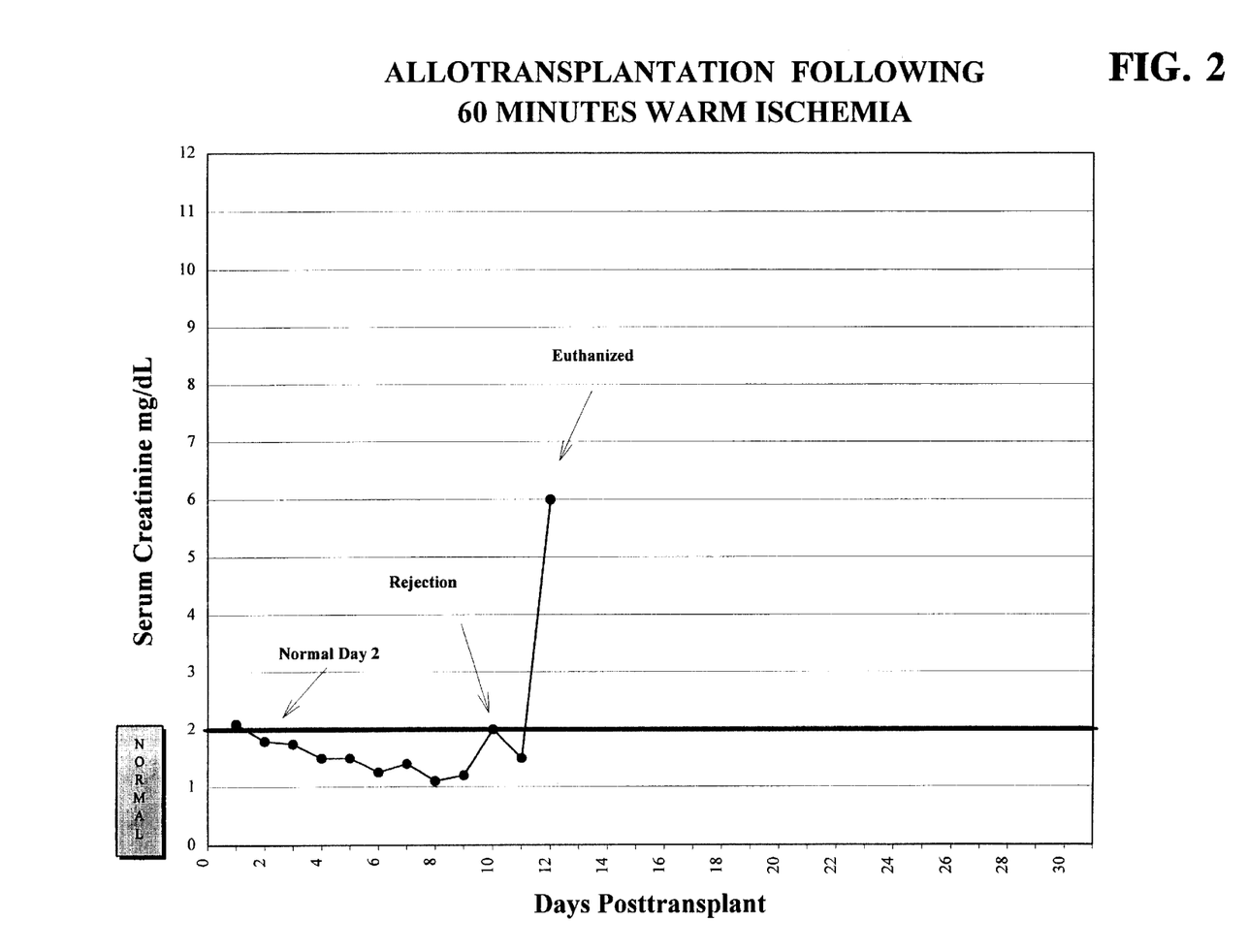
FIG. 2 is a graph of an organ function parameter (serum creatinine) related to the number of days posttransplant in a canine allotransplantation using the process and resuscitation solution according to the present invention.
Figure 3:
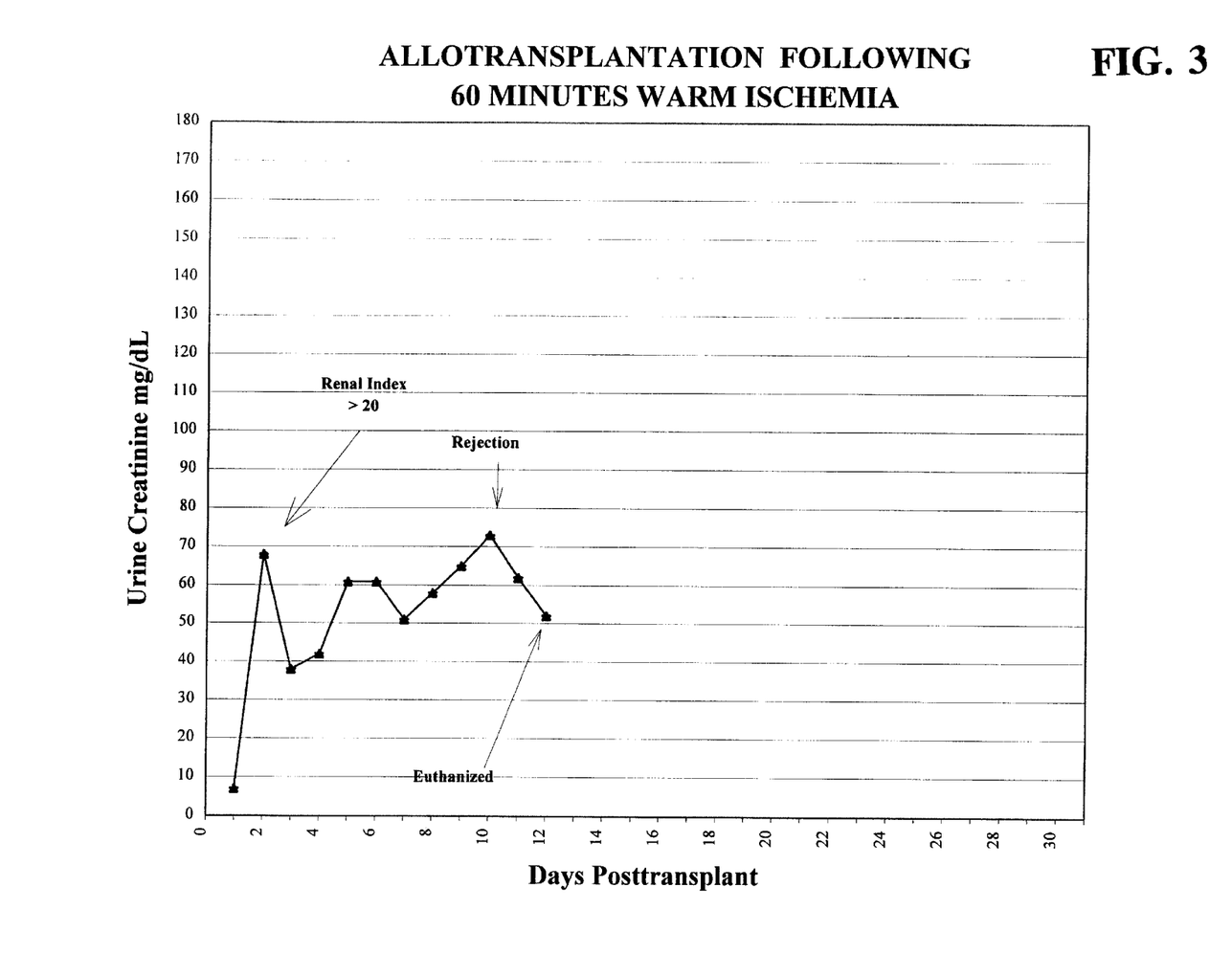
FIG. 3 is a graph of an organ function parameter (urine creatinine) related to the number of days posttransplant in a canine allotransplantation using the process and resuscitation solution according to the present invention.

An organ resuscitated using the process and resuscitation solution according to the present invention was evaluated for in vivo function subsequent to resuscitation. A canine allotransplantation was performed allowing for a period of blood flow deprivation of 60 minutes postmortem, removing a kidney from a canine donor; flushing the organ with the resuscitation solution according to the present invention; and perfusing the organ for 2 hours, using the process and resuscitation solution according to the present invention, at 30° to 32° C. Following the resuscitation process, the kidney was then allotransplanted into a canine recipient with a simultaneous bilateral nephrectomy of the recipient's kidneys. Therefore, the canine recipient was dependent on the resuscitated kidney for survival. The posttransplant course of the canine recipient is shown in FIGS. 2 & 3.

The kidney reperfused well and produced urine within two hours of transplantation. The kidney continued to produce urine throughout the observed posttransplant period. As shown in FIG. 2, the recipient experienced a slight rise in serum creatinine to a level of over 2 mg/dl at 24 hours posttransplant. The serum creatinine returned to a normal range within 48 hours posttransplant. The serum chemistries remained normal until the tenth day posttransplant, when acute organ rejection occurred (insufficient immunosuppression regimen was administered to the canine recipient). As shown in FIG. 3, the urinary creatinine value quickly rose and was within a normal range of approximately 70 mg/dl within 48 hours posttransplant. This very mild episode of acute tubular necrosis (ATN) occurring initially, was rapidly reversed within 48 hours posttransplant. The reversible nature of the acute tubular necrosis, along with the ability of the transplanted kidney to support the recipient's continued survival, demonstrated the viability and in vivo function of the transplanted organ which had suffered more than 60 minutes of warm ischemia. Thus, an organ resuscitated using the process and resuscitation solution according to the present invention, can function in vivo subsequent to resuscitation.

B. Autotransplantation

Figure 4:
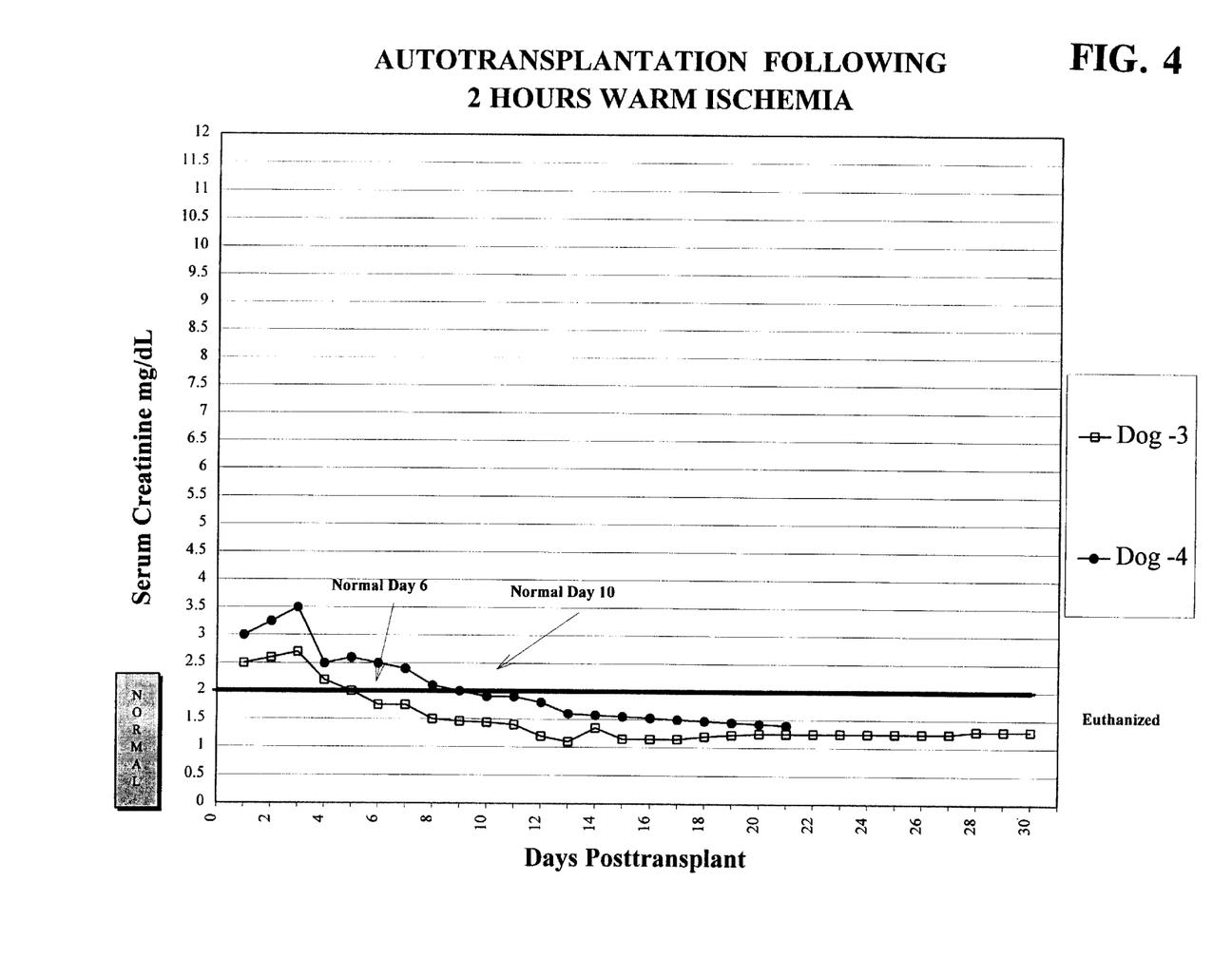
FIG. 4 is a graph of an organ function parameter (serum creatinine) related to the number of days posttransplant in a canine autotransplantation using the process and resuscitation solution according to the present invention.
Figure 5:
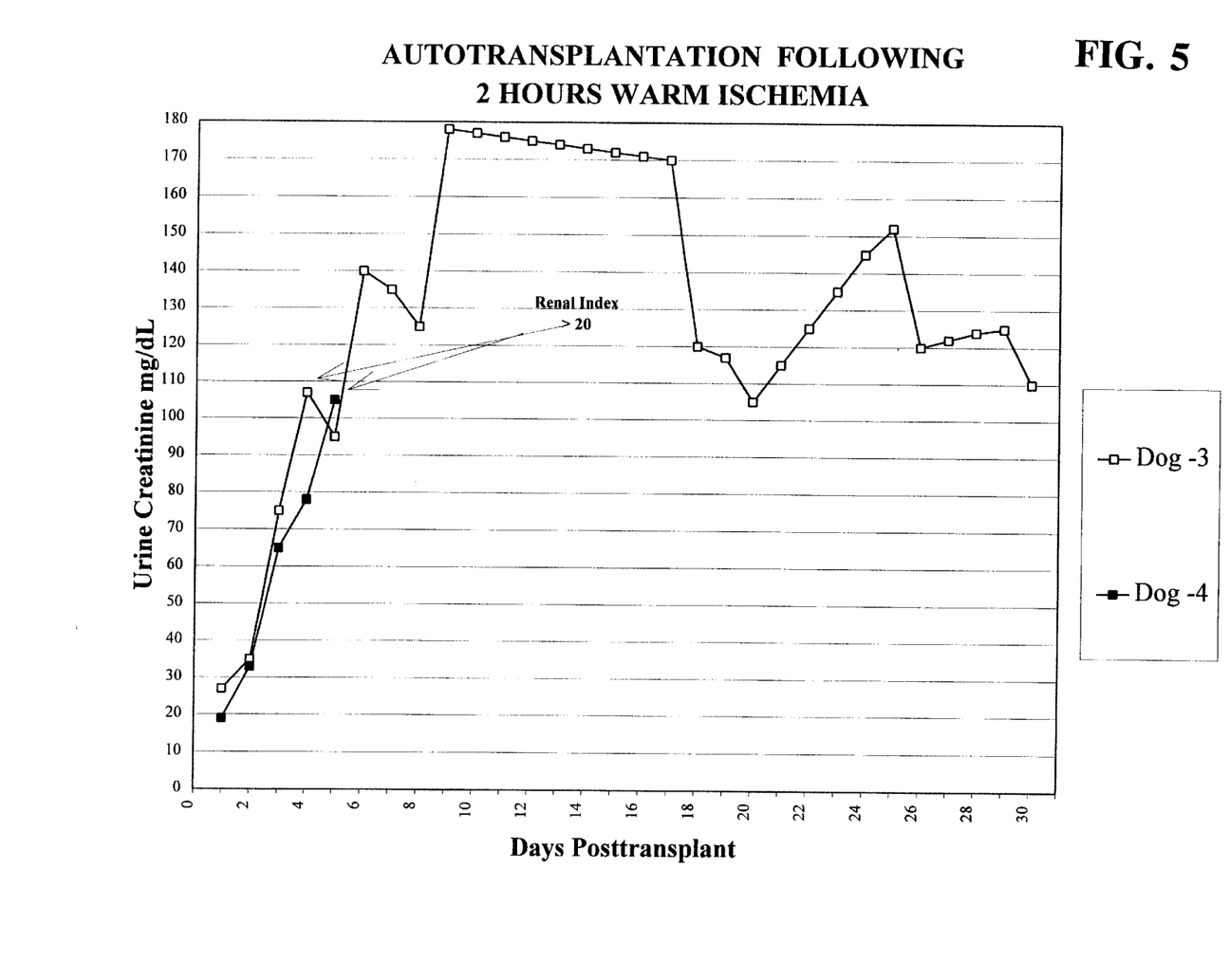
FIG. 5 is a graph of an organ function parameter (urine creatinine) related to the number of days posttransplant in a canine autotransplantation using the process and resuscitation solution according to the present invention.

In another embodiment, an organ resuscitated using the process and resuscitation solution according to the present invention was evaluated for in vivo function subsequent to resuscitation. Using two dogs, a canine autotransplantation was performed by removing the left kidneys, which were then warm ischemically damaged in a 37° C. saline bath for 2 hours. Following the period of warm ischemia, the kidneys were cannulated and flushed with the resuscitation solution according to the present invention; and perfused for 2 hours, using the process and resuscitation solution according to the present invention, at 30° to 32° C. Following the resuscitation process, the kidneys were auto-transplanted with a simultaneous nephrectomy of the untreated, contralateral kidney. Therefore, each recipient dog was solely dependent on the resuscitated kidney for its survival. The posttransplant course of the recipient dogs is shown in FIGS. 4 & 5.

The kidneys reperfused well and produced urine within hours of transplantation. The kidneys continued to produce urine throughout the observed posttransplant period. As shown in FIG. 4, both dogs experienced a slight rise in serum creatinine consistent with ATN. In each case, a peak serum creatinine value occurred on the third day posttransplant with values of 3.5 mg/dl and 2.8 mg/dl, respectively. However, the serum creatinine levels returned to a normal range within the tenth day post-transplant. The serum chemistries remained normal for the remainder of the observed posttransplant period. As shown in FIG. 5, the urinary creatinine value quickly rose and was within a normal range several days prior to the normalization of the serum chemistries. Upon euthanasia, the histologic findings revealed essentially normal kidneys. These findings are indicative of regeneration of the tubular epithelium. The reversible nature of the acute tubular necrosis, along with the ability of the transplanted kidney to support the recipient's continued survival, demonstrated the viability and in vivo function of the transplanted organ which had suffered more than 2 hours of warm ischemia. Thus, an organ resuscitated using the process and resuscitation solution according to the present invention, can function in vivo subsequent to resuscitation.

EXAMPLE 7

Comparison With Known Preservation Solutions

Organs were resuscitated using either the process and resuscitation solution according to the present invention, or a preservation solution known in the art (either a basal culture medium- RSM-210™, or VIASPAN™), and then compared for function and histology. Each group of kidneys suffering from 60 minutes of blood flow deprivation was flushed at 32° C. using the respective solution, and then perfused 2 hours with the respective solution: VIASPAN™ at 4° C.; or RSM-210™ or the resuscitation solution according to the present invention at 30°–32° C., using the same process for resuscitation. A comparison of the mean perfusion characteristics (pressure; flow rate; and vascular resistance) and organ function (urine creatinine concentration; histology) of kidneys deprived of blood flow for 60 minutes and treated with the respective solution is shown in Table 5.

TABLE 5

| Parameter | Resuscitation Solution | RSM-210 ™ | ViaSpan ™ |
| --- | --- | --- | --- |
| pressure (mmHg) | 54/25 | 44/40 | 54/46 |
| flow rate (cc/min) | 97.4 | 12.9 | 27 |
| vascular resistance | 0.47 | 3.25 | 1.8 |
| creatinine (mg/dl) | 41.8 | no urine | no urine |
| histology | well preserved | well preserved | glomeruli swelling, early tubular necrosis |

The results shown in Table 5 demonstrate that the resuscitation solution according to the present invention has superior ability, compared to RSM-210™ and VIASPAN™, in restoring vascular characteristics, as well as function in ischemically damaged organs. For example, kidneys flushed and perfused using the resuscitation solution according to the present invention in the resuscitation process desirably showed reduced vasoconstriction, and higher flow rates compared to those flushed and perfused with RSM-210™ or VIASPAN™. Similarly, the kidneys flushed and perfused using the resuscitation solution according to the present invention were the only kidneys in which organ function was restored, resulting in production of urine with concordant secretion of creatinine. Histologically, only the kidneys flushed and perfused using the resuscitation solution according to the present invention or with RSM-210™, were restored and preserved sufficiently as indicated by the well preserved renal architecture. In contrast, those kidneys flushed and perfused with VIASPAN™ solution demonstrated evidence of histological damage including glomeruli swelling and tubular necrosis. Demonstrated is the superior ability, as compared to preservation solutions known to those skilled in the art, of the process and resuscitation solution according to the present invention to overcome the effects of warm ischemia in organs, and support a repair process to the degree that impairment of organ function can be reversed.

EXAMPLE 8

Oxygen Delivery In The Resuscitation Process

As discussed in detail previously, one embodiment of the present invention is to include as a component in the formulation of the resuscitation solution one or more oxygen carrying agents. Evaluated were the effects of various oxygen carrying agents as a component in the resuscitation solution, and their relative role of molecular oxygen delivery; and the ability of the process and resuscitation solution according to the present invention to support ongoing oxidative metabolism. The resuscitation solution not supplemented with an oxygen carrying agent (in Table 6, noted as "IRS"), the resuscitation solution supplemented with washed red blood cells (in Table 6, noted as "RS-RBC";

15% v/v), the resuscitation solution supplemented with purified hemoglobin (in Table 6, noted as "IRS-Hgb"; 60 cc/liter of a commercial preparation), and the resuscitation solution supplemented with perfluorochemical emulsion (in Table 6, noted as "Rs-Pf"; 20% v/v) were each used to resuscitate kidneys suffering from 60 minutes of warm ischemia. Each group of kidneys suffering from 60 minutes of blood flow deprivation was flushed at 30° to 32° C. using the respective solution, and then perfused at 30° to 32° C. for 2 hours with the respective solution using the same process for resuscitation. A comparison of the mean perfusion characteristics (pressure; flow rate; and vascular resistance) and organ function (urine creatinine concentration; histology) of kidneys deprived of blood flow for 60 minutes and treated with the respective solution is shown in Table 6.

TABLE 6

| Solution | pressure (mmHg) | flow rate (cc/min) | Vascular resist. | Creatinine | Histology |
|---|---|---|---|---|---|
| RS | 54/38 | 92.3 | 0.50 | 8.4 | well preserved |
| RS-RBC | 56/36 | 98.2 | 0.58 | 8.3 | well preserved |
| RS-Hgb | 58/42 | 66.67 | 0.75 | 18 | well preserved |
| RS-Pf | 54/25 | 97.4 | 0.47 | 41.8 | well preserved |

The results shown in Table 6 demonstrate that as the concentration of molecular oxygen is increased in the resuscitation solution, via a more efficient oxygen carrying agent as a component in the resuscitation solution, the organ function is improved as a result of the resuscitation process. For example, efficient oxygen carrying agents perfluorochemical or purified hemoglobin result in a higher concentration of molecular oxygen delivered during the process. Function of kidneys treated with the resuscitation solution containing either of these carrying agents is improved over that of kidneys treated with resuscitation solution lacking an added oxygen carrying agent, or containing a less efficient oxygen carrying agent. For example, using the resuscitation solution with either purified hemoglobin or perfluorochemical according to the present invention resulted in a mean urine creatinine concentration of 18 mg/dl and 41.8 mg/dl, respectively. In contrast, when an oxygenator is not used in the resuscitation process and the resuscitation solution lacks an oxygen carrying agent, or contains a low concentration washed red blood cells, the mean urinary creatinine is 8.4 mg/dl and 8.3 mg/dl, respectively. Demonstrated is another embodiment of the resuscitation solution in which, by the addition of one or more efficient oxygen carrying agents as a component in the solution, improved organ function is noted in an ischemically damaged organ treated by the process of the present invention.

EXAMPLE 9

The process and resuscitation solution according to the present invention can be used to overcome the effects of warm ischemia in liver deprived of blood flow, and support a repair process to the degree that impairment of liver function can be reversed. While the length of time necessary for perfusion can depend on the length of time of blood flow deprivation, treatment of an ischemically damaged liver with the process (flushing and perfusing) according to the present invention for approximately 2 hours may be sufficient in the resuscitation of most livers (e.g., deprived of blood flow for between about 0.5 to 4 hours) for resumption of organ function. Overall liver function, as well as individual aspects of physiology of the liver, can be determined by measuring concentrations of constituents in both the circulated perfusate, and the liver product (bile). Functional characteristics of liver can be assessed by measuring parameters including, but not limited to, bile concentrations of bile salts, cholesterol, alkaline phosphatase; bile pH; and liver vascular flow rate, oxygen consumption, and glucose utilization (as measured from the perfusate). Thus, in accordance with the process and solutions as illustrated in Examples 1 and 2, ischemically damaged liver may be treated and then prospectively assessed for metabolic function.

EXAMPLE 10

The process and resuscitation solution according to the present invention can be used to overcome the effects of warm ischemia in pancreas deprived of blood flow, and support a repair process to the degree that impairment of pancreas function can be reversed. While the length of time necessary for perfusion can depend on the length of time of blood flow deprivation, treatment of an ischemically damaged pancreas with the process (flushing and perfusing) according to the present invention for approximately 2 hours may be sufficient in the resuscitation of most pancreas (e.g., deprived of blood flow for between about 0.5 to 4 hours) for resumption of organ function. Overall pancreatic function, as well as individual aspects of physiology of the pancreas, can be determined by measuring concentrations of constituents in both the circulated perfusate, and the pancreas. Functional characteristics of the pancreas include pancreatic enzyme concentrations such as amylase, lipase; the hormone insulin; pancreatic secretion pH, sodium and potassium; and pancreas vascular flow rate, oxygen consumption, and glucose utilization (as measured from the perfusate). Thus, in accordance with the process and solutions as illustrated in Examples 1 and 2, ischemically damaged pancreas may be treated and then prospectively assessed for metabolic function.

EXAMPLE 11

The process and resuscitation solution according to the present invention can be used to overcome the effects of warm ischemia in a heart deprived of blood flow, and support a repair process to the degree that impairment of heart function can be reversed. While the length of time necessary for perfusion can depend on the length of time of blood flow deprivation, treatment of an ischemically damaged heart with the process (flushing and perfusing) according to the present invention for approximately 2 hours may be sufficient in the resuscitation of most hearts (e.g., deprived of blood flow for between approximately 0.5 to 4 hours) for resumption of organ function. Overall cardiac function, as well as individual aspects of physiology of the heart, can be determined by measuring concentrations of constituents in both the circulated perfusate, and the heart. Functional characteristics of heart can be assessed by measuring parameters including, but not limited to, mechanical and electrical work, heart enzymes such as transaminases (aspartate aminotransferase, AST), lactate dehydrogenase (LD), fructose 1,6-diphosphate aldolase (ALS), malate dehydrogenase (MD), glutathione reductase (GR), creatine phosphokinase (CPK), hydroxybutyrate dehydrogenase (HBD); heart vascular flow rate, oxygen consumption, and glucose utilization (as measured from the perfusate). Thus, in accordance with the process and solutions as illustrated in Examples 1 and 2, ischemically damaged heart may be treated and then prospectively assessed for metabolic function.

EXAMPLE 12

The process and resuscitation solution according to the present invention can be used to overcome the effects of warm ischemia in a small bowel deprived of blood flow, and support a repair process to the degree that impairment of small bowel function can be reversed. While the length of time necessary for perfusion can depend on the length of time of blood flow deprivation, treatment of an ischemically damaged small bowel with the process (flushing and perfusing) according to the present invention for approximately 2 hours may be sufficient in the resuscitation of most small bowels (e.g., deprived of blood flow for between approximately 0.5 to 4 hours) for resumption of organ function. Overall bowel function, as well as individual aspects of physiology of the small bowel, can be determined by measuring concentrations of constituents in both the circulated perfusate, and the small bowel. Functional characteristics of small bowel can be assessed by measuring parameters including, but not limited to, functional assays such as gastric acid stimulation tests, and absorption assays using tracer molecules; small bowel vascular flow rate, oxygen consumption, and glucose utilization (as measured from the perfusate). Thus, in accordance with the process and solutions as illustrated in Examples 1 and 2, ischemically damaged small bowel may be treated and then prospectively assessed for metabolic function.

EXAMPLE 13

The process and resuscitation solution according to the present invention can be used to overcome the effects of warm ischemia in a lung deprived of blood flow, and support a repair process to the degree that impairment of lung function can be reversed. It may be desirable to first treat the lung transplant with surfactant just before reperfusion (See, e.g. Erasmus et al., 1996, *Am. J. Respir. Crit. Care Med.* 153:665–670). While the length of time necessary for perfusion can depend on the length of time of blood flow deprivation, treatment of an ischemically damaged lung with the process (flushing and perfusing) according to the present invention for approximately 2 hours may be sufficient in the resuscitation of most lungs (e.g., deprived of blood flow for between approximately 0.5 to 4 hours) for resumption of organ function. Overall lung function, as well as individual aspects of physiology of the lung, can be determined by measuring concentrations of constituents in the circulated perfusate such as surfactant protein A (SP-A) levels. Pulmonary functional characteristics can be assessed by measuring parameters including, but not limited to, FVC (forced vital capacity), FEV1 (forced expiratory volume in 1 second), PEFR (peak expiratory flow rate), VA (mean alveolar volume), TLC (total lung capacity), and DLCO (transfer for carbon monoxide). Thus, in accordance with the process and solutions as illustrated in Examples 1 and 2, ischemically damaged lung may be treated and then prospectively assessed for metabolic function.

It should be understood that the embodiments and the examples of the present invention, as described herein, are for purposes of illustration only, and not limitation, and any changes or modifications as will become apparent to one of ordinary skill in the art from the foregoing description and accompanying figures are intended to be included within the scope of the appended claims and the equivalents thereof.

What is claimed is:

1. A process for inducing repair of an ischemically damaged organ to the degree that impairment of organ function can be reversed, said process comprises flushing the organ at a temperature of about 28° C. to about 37° C. with a buffered physiological solution to remove blood and acidotic products which have accumulated in the organ during blood flow deprivation; and perfusing the organ at a temperature of about 28° C. to about 37° C. with a buffered physiological solution which further comprises a means for dilating blood vessels within the organ, a means for reestablishing cellular integrity and cellular function thereby restoring organ function, and a means for reestablishing oxidative metabolism in the organ in readapting the organ to an oxygenated environment.

2. The process according to claim 1, wherein the buffered physiological solution for perfusing the organ further comprises a means for preventing organ tissue damage during restoration of blood circulation to the organ.

3. The process according to claim 1, wherein the means for reestablishing oxidative metabolism comprises introducing molecular oxygen by a mode selected from the group consisting of an oxygenator and an oxygen carrying agent.

4. The process according to claim 1, wherein the perfusion is performed using a device comprising a laminar or pulsatile pumping system to deliver the buffered physiological solution, and said device further includes a means for providing and controlling perfusion and perfusion pressure; a means for temperature control; a means for providing and controlling introduction of, and venting of, respiratory gases; and a means for testing or collecting for testing the buffered physiological solution which has already perfused through the organ to monitor and measure a functional characteristic selected from the group consisting of pH, various pressures, flow rate, vascular resistance, chemical constituents, oxygenation, carbon dioxide concentration, oxygen consumption, and a combination thereof.

5. The process according to claim 4, wherein the perfusion is performed using a second device, in conjunction with the first device, to test or collect for testing an organ product diverted from the organ, wherein subsequent measurement of parameters of the organ product relate to organ integrity and function.

6. A process for inhibiting ischemic damage, and for inducing repair of ischemic damage to a degree that impairment of organ function is reversed in an organ deprived of blood flow, said process is performed at a temperature of about 28° C. to about 37° C. and comprises:

(a) flushing the organ with a buffered physiological solution which removes blood and acidotic products having accumulated in the organ during blood flow deprivation, and further comprises a means for restoring the organ to a physiologic pH, a means for vasodilating microvessels in the organ, a means to supporting ongoing anaerobic metabolism, a means for initiating a conversion from anaerobic metabolism to oxidative metabolism, and metabolites for recovering cellular integrity and cellular function; and (b) perfusing the organ with a buffered physiological solution which further comprises a means for normalizing organ oxygenation, organ temperature, and organ pH, a means for vasodilating vasculature of the organ, and metabolites for recovery of cellular integrity and cellular function.

7. The process according to claim 6, wherein the buffered physiological solution for perfusing the organ further comprises a means for preventing organ tissue damage during restoration of blood circulation to the organ.

8. The process according to claim 6, wherein the means for reestablishing oxidative metabolism comprises introducing molecular oxygen by a mode selected from the group consisting of an oxygenator or an oxygen carrying agent.

9. The process according to claim 6, wherein the perfusion is performed using a device comprising a laminar or pulsatile pumping system to deliver the buffered physiological solution, and said device further includes a means for providing and controlling perfusion and perfusion pressure; a means for temperature control; a means for providing and controlling introduction of, and venting of, respiratory gases; and a means for testing or collecting for testing the buffered physiological solution which has already perfused through the organ to monitor and measure a functional characteristic selected from the group consisting of pH, various pressures, flow rate, vascular resistance, chemical constituents, oxygenation, carbon dioxide concentration, oxygen consumption, and a combination thereof.

10. The process according to claim 9, wherein the perfusion is performed using a second device, operatively associated with the first device, to test or collect for testing an organ product diverted from the organ, wherein subsequent measurement of parameters of the organ product relate to organ integrity and function.

11. A resuscitation solution at a warm temperature of about 28° C. to about 37° C. for inhibiting ischemic damage, and for inducing repair of ischemic damage to a degree that impairment of organ function is reversed in an organ deprived of blood flow, said resuscitation solution comprises a buffered physiological solution and further comprises:

vasodilators in a physiologically effective amount for dilating vasculature of the organ;

chemical energy substrates in a physiologically effective amount to reestablish oxidative metabolism lost during organ blood flow deprivation; and trophic factors in a physiologically effective amount to promote one or more cellular repair processes to reestablish cellular function lost during organ blood flow deprivation, wherein the trophic factors promote protein synthesis leading to reestablishment of tighter cellular junctions and regeneration of membrane polarity.

12. The resuscitation solution according to claim 11, wherein the vasodilators comprise a combination of components selected from the group consisting of substrates for endothelial cell-mediated vasodilation, substrates for microvessel vasodilation, calcium channel blockers.

13. The resuscitation solution according to claim 12, wherein the resuscitation solution comprises substrates for endothelial cell-mediated vasodilation, substrates for microvessel vasodilation, and calcium channel blockers, wherein the substrates for endothelial cell-mediated vasodilation comprise acetylcholine and arginine, wherein the substrates for microvessel vasodilation comprise prostacyclin and $Mg^+$, and wherein the calcium channel blockers comprise adenosine and verapamil.

14. The resuscitation solution according to claim 11, wherein the chemical energy substrates comprise a combination of components selected from the group consisting of components of the adenine compound pool, components of the citric acid cycle, and components of the coupled electron transport chain.

15. The resuscitation solution according to claim 14, wherein the chemical energy substrates are selected from the group consisting of pyruvate, glucose, ATP, AMP, coenzyme A, β-nicotinamide adenine dinucleotide ($Nad^+$), flavin adenine dinucleotide (FAD), thiamine pyrophosphate chloride (cocarboxylase), UTP, chloride, magnesium, and a combination thereof.

16. The resuscitation solution according to claim 11, wherein the trophic factors are selected from the group consisting of amino acids, magnesium, nucleic acid derivatives, ribonucleosides, acidic fibroblast growth factor (FGF), basic FGF, heparin, chondroitin sulfate, and a combination thereof.

17. The resuscitation solution according to claim 11, wherein the solution further comprise a physiologically effective amount of a component selected from the group consisting of an antioxidant, an oxygen carrying agent, and a combination thereof.

18. The resuscitation solution according to claim 11, wherein the solution further comprise a pharmaceutically effective amount of a neuroprotective drug.

19. A process for inducing repair of an ischemically damaged organ to the degree that impairment of organ function can be reversed, said process being performed at a temperature of about 28° C. to about 37° C. and comprises flushing the organ and perfusing the organ with the resuscitation solution according to claim 11.

20. A process for inducing repair of an ischemically damaged organ to the degree that impairment of organ function can be reversed, said process being performed at a temperature of about 28° C. to about 37° C. and comprises flushing the organ and perfusing the organ with the resuscitation solution according to claim 17.

21. A process for inhibiting ischemic damage, and for inducing repair of ischemic damage to a degree that impairment of organ function is reversed in an organ deprived of blood flow, said process is performed at a temperature of about 28° C. to about 37° C. and comprises flushing the organ and perfusing the organ with the resuscitation solution according to claim 11.

22. A process for inhibiting ischemic damage, and for inducing repair of ischemic damage to a degree that impairment of organ function is reversed in an organ deprived of blood flow, said process is performed at a temperature of about 28° C. to about 37° C. and comprises flushing the organ and perfusing the organ with the resuscitation solution according to claim 17.

23. A process for preparing a solution for inhibiting ischemic damage, and for inducing repair of ischemic damage to a degree that impairment of organ function is reversed in an organ deprived of blood flow, said process being performed at a warm temperature of about 28° C. to about 37° C. and comprising adding to a buffered physiological solution a combination of supplements, wherein the supplements comprise: vasodilators in a physiologically effective amount for dilating vasculature of the organ; chemical energy substrates in a physiologically effective amount to reestablish oxidative metabolism lost during organ blood flow deprivation; and trophic factors in a physiologically effective amount to promote one or more cellular repair processes to reestablish cellular function lost during organ blood flow deprivation; and wherein the solution is adjusted to a pH with a pH range of from about 6.5 to about 7.5, and has an osmolarity greater than 330 mOsm.

24. The process according to claim 23, wherein the vasodilators comprise a combination of components selected from the group consisting of substrates for endothelial cell-mediated vasodilation, substrates for microvessel vasodilation, calcium channel blockers, and a combination thereof.

25. The process according to claim 24, wherein the resuscitation solution comprises substrates for endothelial cell-mediated vasodilation, substrates for microvessel vasodilation, and calcium channel blockers, wherein the substrates for endothelial cell-mediated vasodilation comprise acetylcholine and arginine, wherein the substrates for microvessel vasodilation comprise prostacyclin and $Mg^+$, and wherein the calcium channel blockers comprise adenosine and verapamil.

26. The process according to claim 23, wherein the chemical energy substrates comprise a combination of components selected from the group consisting of components of the adenine compound pool, components of the citric acid cycle, and components of the coupled electron transport chain.

27. The process according to claim 26, wherein the chemical energy substrates are selected from the group consisting of pyruvate, glucose, ATP, AMP, coenzyme A, β-nicotinamide adenine dinucleotide ($Nad^+$), β-nicotinamide adenine trinucleotide (NADH), flavin adenine dinucleotide (FAD), thiamine pyrophosphate chloride (cocarboxylase), UTP, chloride, magnesium, and a combination thereof.

28. The process according to claim 23, wherein the trophic factors are selected from the group consisting of amino acids, magnesium, nucleic acid derivatives, ribonucleosides, acidic fibroblast growth factor (FGF), basic FGF, heparin, chondroitin sulfate, and a combination thereof.

29. The process according to claim 23, wherein the supplements further comprise a physiologically effective amount of a component selected from the group consisting of an antioxidant, an oxygen carrying agent, and a combination thereof.

30. The process according to claim 23, wherein the supplements further comprise a pharmaceutically effective amount of a neuroprotective drug.

* * * * *

UNITED STATES PATENT AND TRADEMARK OFFICE
CERTIFICATE OF CORRECTION

PATENT NO. : 5,843,024
DATED : December 1, 1998
INVENTOR(S) : Lauren Brasile

It is certified that error appears in the above-identified patent and that said Letters Patent is hereby corrected as shown below:

ON THE TITLE PAGE:
ITEM [54] Title

"SOLUTION AND PROCESS FOR RESUSCITATION AND PREPARATION OF ISCHEMICALLY DAMAGED TISSUE"

should read

--SOLUTION AND PROCESS FOR RESUSCITATION AND REPARATION OF ISCHEMICALLY DAMAGED TISSUE--.

Signed and Sealed this

Tenth Day of August, 1999

*Attest:*

Q. TODD DICKINSON

*Attesting Officer*     Acting Commissioner of Patents and Trademarks